United States Patent [19]

Ward

[11] Patent Number: 4,709,111
[45] Date of Patent: Nov. 24, 1987

[54] OLIGOMERIZATION PROCESS WITH INTEGRATED HEAT UTILIZATION

[75] Inventor: Dennis J. Ward, South Barrington, Ill.

[73] Assignee: UOP Inc., Des Plaines, Ill.

[21] Appl. No.: 19,824

[22] Filed: Feb. 27, 1987

[51] Int. Cl.$^4$ .................................................. C07C 2/02
[52] U.S. Cl. .................................. 585/503; 585/520; 585/911
[58] Field of Search ......................... 585/503, 911, 520

[56] References Cited

U.S. PATENT DOCUMENTS

| | | | |
|---|---|---|---|
| 2,104,296 | 1/1938 | Frey | 196/10 |
| 3,478,124 | 11/1969 | Fernald et al. | 585/503 |
| 4,334,118 | 6/1982 | Manning | 585/529 |
| 4,384,157 | 5/1983 | DeGraff | 585/514 |
| 4,456,781 | 6/1984 | Marsh et al. | 585/533 |

OTHER PUBLICATIONS

Hengstebeck, R. J., "Petroleum Processing, Principles and Applications," McGraw-Hill Book Co., Inc., 1959, pp. 208-218.

*Primary Examiner*—Curtis R. Davis
*Attorney, Agent, or Firm*—Thomas K. McBride; John F. Spears, Jr.

[57] ABSTRACT

A process flow for a catalytic oligomerization process is presented. The feed contacts a solid catalyst in a tubular reactor cooled by indirect heat exchange. The mixed-phase coolant used in the reactor is the reactor effluent itself, which has been cooled by indirect heat exchange and depressurized. The reactor effluent is then passed into a rectified separation zone. The heat picked up by the effluent stream in the reactor is thereby used in separating light hydrocarbons from the effluent to produce a recycle stream.

15 Claims, 1 Drawing Figure

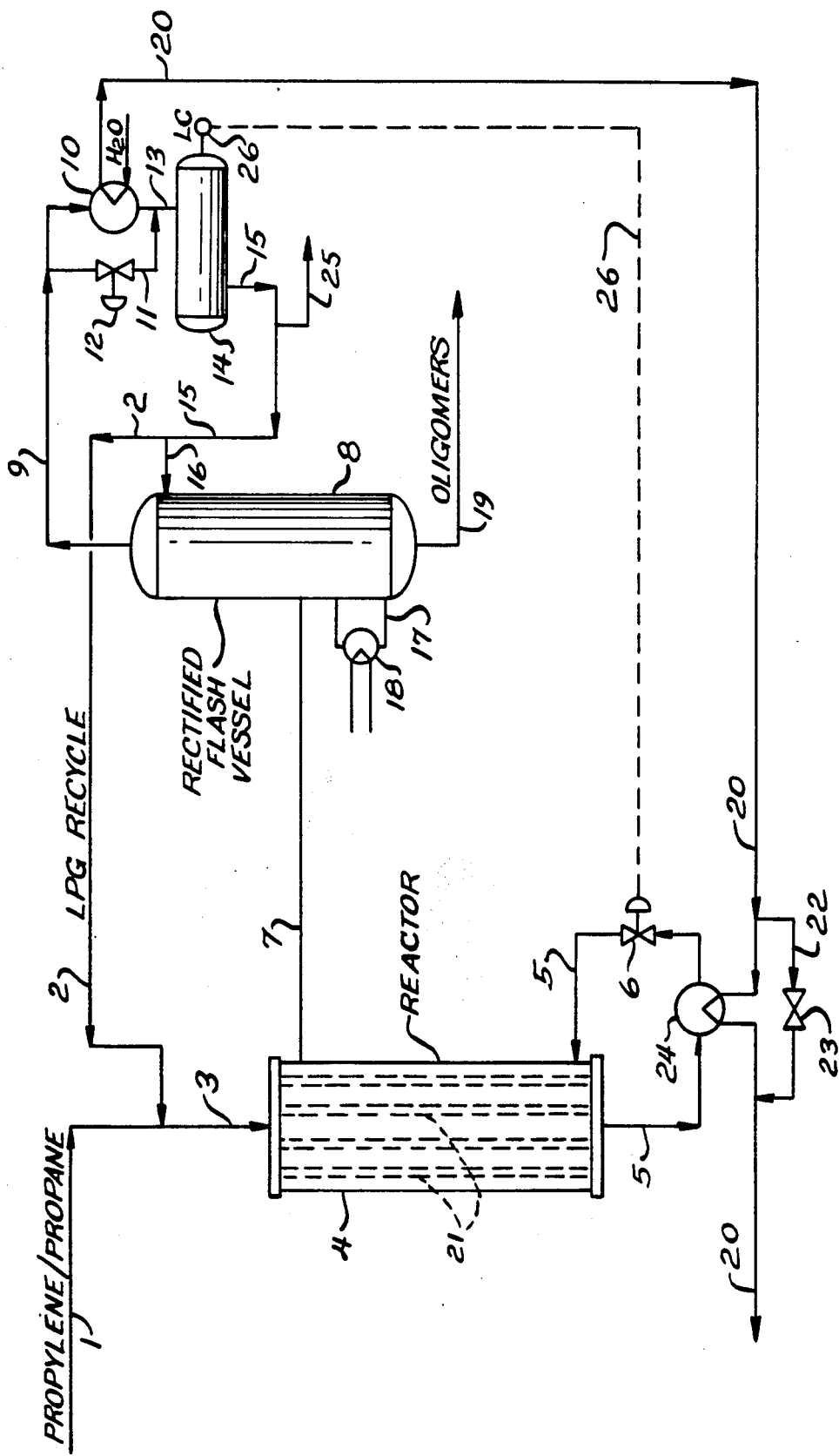

OLIGOMERIZATION PROCESS WITH INTEGRATED HEAT UTILIZATION

FIELD OF THE INVENTION

The invention relates to the removal of heat from the reaction zone of an exothermic hydrocarbon conversion process, commonly referred to as catalytic condensation, in which light olefinic hydrocarbons are reacted to produce heavier hydrocarbons. The invention more directly relates to the catalytic condensation or oligomerization of propylene contained in a mixed propane-propylene feed stream to produce $C_6$-plus acyclic hydrocarbons which are suitable for use as motor fuels including gasoline. The invention is specifically concerned with providing a method of controlling the temperature in the reaction zone used in a catalytic condensation process through the use of a circulating coolant media.

INFORMATION DISCLOSURE

The catalytic condensation or oligomerization of light olefins is an established commercial process used to produce gasoline blending components. It is described at pages 208 to 218 of "Petroleum Processing, Principles and Applications" by R. J. Hengstebeck, McGraw-Hill Book Co., Inc., 1959. This description includes a drawing at page 212 which shows the effluent of the reaction zone being passed into a depropanizer column, with a first portion of the depropanizer net overhead stream being recycled to the reaction zone and a second portion being withdrawn from the process. The net bottoms stream of the depropanizer is passed into a debutanizer column. This reference also indicates propylene is a satisfactory feedstock and that mixtures of paraffins and olefins are the normal reaction zone charge stock.

This same reference describes the use of tubular reactors at page 215. A coolant, such as water, is circulated over the outside of catalyst filled tubular reactors which form a single pass heat exchanger. The coolant may be allowed to vaporize, with temperature being controlled by controlling the pressure of the vapor.

U.S. Pat. No. 4,384,157 issued to R. R. DeGraff is pertinent for its showing of a product recovery and separation system which may be employed to recover $C_6+$ hydrocarbons from the effluent of a catalytic condensation zone employing a mixed feed of propane and propylene. This reference illustrates the recycling of a portion of a product separation zone overhead stream which is rich is propane to the reaction zone by admixture with the feedstream. U.S. Pat. No. 4,456,781 issued to S. K. Marsh et al is pertinent for its showing of an oligomerization process wherein the reactants are cooled between each of several reactors used in series by employing heat available in the reactants to reboil a fractionation column. To achieve this the reactants are passed through the reboiler of the column and then returned to the process flow. This reference also describes the tubular and chamber type reactor structures which may be used in oligomerization reactions.

U.S. Pat. No. 4,334,118 issued to J. F. Manning is believed pertinent for its description of the use of quench in the form of propane or recycled unreacted feed for the purpose of temperature control within the polymerization reaction zone.

U.S. Pat. No. 2,104,296 issued to F. E. Frey relates to a thermal or high pressure conversion of olefinic hydrocarbons to larger molecules. This process is achieved by subjecting the feed to extreme pressures of above 1000 psig (6895 k Pa or 69 bar) with pressures above 5000 psig (34475 k Pa or 345 bar) being specified as favorable for the reaction. A part of the effluent of the tubular reactor may be recycled through line 17 to maintain the reactor tubes at a desired operating temperature. This stream of "still hot reacted hydrocarbons" serves to both heat entering reactants and to remove heat liberated by the reaction. The recycled portion of the effluent is not cooled, depressurized or partially vaporized prior to entering the reactor.

BRIEF SUMMARY OF THE INVENTION

The invention provides an improved process for the catalytic oligomerization of propylene contained in a propylene-propane mixture or the catalytic oligomerization of butylene contained in a butylene-butane admixture. The subject invention provides a highly economic and effective method of cooling the oligomerization reactor and simultaneously supplying the energy required for the separation of the unreacted LPG from the reactor effluent for recycling to the reaction zone or withdrawal from the process. By employing the reactor effluent as the reactor coolant stream any concerns about leakage of the reactants through the individual tubular conduits employed within the reactor is eliminated. Furthermore, the heat released within the reactor is transferred to the reactor effluent and is immediately available for use in the separation of the reactor effluent into an LPG recycle stream and an oligomer-containing product stream.

A broad embodiment of the invention may be characterized as a hydrocarbon conversion process which comprises the steps of passing a liquid-phase feed stream comprising a $C_2$–$C_5$ aliphatic feed olefinic hydrocarbon into contact with an oligomerization catalyst within a reaction vessel of an oligomerization zone and producing a reaction zone effluent stream comprising the feed hydrocarbon and a $C_6$-plus product hydrocarbon, with the reaction zone comprising a tubular catalyst retaining means which is in indirect heat exchange relationship with a coolant media which is vertically circulated through the reaction vessel to remove heat released in the oligomerization process, with a portion of the coolant media being vaporized within the reaction vessel; cooling the reaction zone effluent stream by indirect heat exchange against a cooling stream; passing the reaction zone effluent stream through the reaction vessel as said coolant media; and, passing coolant media withdrawn from the reaction vessel into a separation zone operated at conditions effective to separate the entering hydrocarbons into an overhead vapor stream comprising the feed hydrocarbon and a net bottoms liquid stream comprising the product hydrocarbon which is removed from the process as a product stream.

BRIEF DESCRIPTION OF THE DRAWING

The Drawing is a simplified process flow diagram illustrating passage of the propylene-propane feed stream of line 1 into the catalyst containing conduits 21 of the reactor. The reactor effluent is cooled and then returned to the reactor through line 5 to remove heat as it flows over the outside of the conduits 21. The heat picked up in this manner is conveyed with the reactor effluent through line 7 to the rectified flash vessel 8.

DETAILED DESCRIPTION

One form of the catalytic condensation process is the oligomerization of light olefins. Oligomerization processes are useful in converting propylene, butylene or propylene-butylene mixtures into higher molecular weight hydrocarbons of greater economic value. They are used to convert propylene into "trimer" or "tetramer" which may then be used to manufacture detergents. The oligomerization type of catalytic condensation process can also be utilized to produce good quality gasoline blending components from propylene or butylene. It is this latter form of the catalytic condensation process which is the preferred embodiment of the inventive concept, although it may be applied to other forms of catalytic condensation process and possibly to other exothermic processes which produce higher boiling products.

The feed stream to the subject oligomerization process is typically a mixture of the feed olefin(s) and a paraffin or paraffins of the same carbon number. The feed stream to the subject invention may comprise a mixture of propane and propylene, a mixture of butanes and butylenes or a mixture comprising both propylene and butylenes and coboiling paraffins. Preferably, this is a rather pure stream which contains very little (less than 5 mole percent) of any hydrocarbons having other than 3 or 4 carbon atoms per molecule. Any hydrocarbons other than propane and propylene preferably have more than 3 carbon atoms per molecule. The feed stream may therefore comprise a mixture of propylene and up to about 50 mole percent butylene plus associated coboiling paraffins. It is especially preferred that the feed stream contains between about 10 and 65 mole percent propylene. The following description of the inventive concept is cast mainly in terms of consuming the preferred propylene feed but also applies to mixed propylene-butylene or butylene feeds.

The catalytic condensation reaction for gasoline production often does not consume all of the olefin present in the feed stream, and the effluent stream of the reaction zone will therefore comprise a mixture of the unreacted olefin and unreactive paraffins in addition to the products of the catalytic condensation process. The effluent of the reaction zone is normally separated into one or more $C_3$ recycle streams comprising propane and propylene, an off gas or light effluent stream which also comprises both propane and propylene and a $C_5$-plus product or oligomer product stream.

Oligomerization reactions are quite exothermic and release considerable amounts of heat. Catalytically promoted reactions release heat in a more localized manner and more rapidly than pressure driven kinetic type reactions such as used in the previously referred to Frey reference. This localized heat release can cause excessive operating temperatures in the reaction zone which in turn can cause poor product quality and possible deactivation of the catalyst. Therefore, it is necessary to remove the heat released during the oligomerization reaction from the reaction zone in order to control the temperature at which the reactions occur. In the case of the dimerization of propylene this heat amounts to about 500 BTU's per pound of oligomer product. Preferably, this heat is actually removed from the reaction zone rather than being merely offset by the addition of cold quench material at immediate points along the path of the reactants. It is also preferred that the heat is removed in a uniform manner corresponding to its rate of generation such that the reactants and the catalyst beds are maintained at a rather uniform temperature at all points between the reactant inlet and reactant outlet of the catalyst beds. Therefore, heat exchange systems which merely cool the reactants at scattered points along the path of the reactant flow, as by quench stream admixture, are not preferred as they allow the establishment and the maintenance of definite temperature profile(s) within the reaction zone.

It is also desirable that the cooling system employed to remove heat from the reaction zone is flexible enough to accommodate changes in the reactant flow rate or desired operating temperature. Such changes in operating conditions may result from the use of a different catalyst or a change in the composition of the feed stream. It is therefore an objective of the subject invention to provide a method for cooling the reaction zones of an oligomerization process. It is also an objective of the subject invention to provide a highly flexible cooling system for use in oligomerization process reaction zones.

The Drawing illustrates the preferred embodiment of the invention. However, it is not intended to limit the scope of the inventive concept to the particular flow shown in the Drawing or to exclude those other embodiments described herein or which result from the normally expected modification of this one particular flow. The Drawing has been simplified by not illustrating commonly used equipment such as control systems and vessel internals which are not required to convey an understanding of the inventive concept.

Referring now to the Drawing, a liquid phase feed stream comprising an admixture of propylene and propane is fed to the process through line 1 and is admixed with a propane-rich recycle stream from line 2. The admixture of these two streams is passed into the reactor 4 through line 3. The entering reactants are then distributed between a number of tubular-form reaction conduits each containing a fixed bed of solid catalyst. The reactants flow downward through the conduits 21 in contact with the solid catalyst under conditions which effect at least a partial oligomerization of the entering propylene and the production of a reaction zone effluent stream carried by line 5 which comprises propane, any residual unconverted propylene and product propylene oligomers such as $C_6$ and $C_9$ branched chain acyclic hydrocarbons. The reactor effluent stream is cooled in the indirect heat exchange means 24 and is depressured during passage through a valve 6. It is then passed into the shell side of the reactor through line 5.

The partially cooled effluent of the reactor passes through the reactor 4 as a coolant stream passing over the outer surface of the tubular-form catalyst conduits 21. The reactor effluent flowing over the shell (outer) side of the conduits thereby removes the heat of reaction being released by the oligomerization reaction and moderates the temperature of the reactants within the reactor. Because of the lower pressure on the shell side of the reactor portions of the coolant, basically propane and propylene, are preferably vaporized. The slightly warmed and mixed-phase reaction zone or reactor effluent stream is passed through line 7 into a separation vessel 8. In the preferred embodiment this is a rectified flash vessel having a plurality of fractionation trays located in an upper portion of the vessel above the feed point of line 7 into the vessel. A liquid phase stream is withdrawn from the vessel 8 through line 19. The liquid phase material is rich in the product oligomer and is withdrawn from the process as the product stream.

Vapor phase material passes upward through the flash vessel countercurrent to descending liquids, with the remaining vaporous material exiting the top of the flash vessel through line 9 as an overhead vapor stream. The overhead vapor stream is at least partially condensed by passage through an indirect heat exchange means 10. A portion of the overhead vapor stream may bypass the heat exchange means 10 through line 11 at a rate controlled by valve 12. The resultant condensate and any bypassed overhead material will enter the overhead receiver 14 through line 13. The material entering the overhead receiver from line 9 will basically comprise $C_3$ hydrocarbons and will be predominantly propane. A liquid phase comprising the propane and normally a small amount of propylene is withdrawn from the overhead receiver 14 through line 15. If desired, a portion of this material may be withdrawn from the process through optional line 25 at a rate set to prevent the accumulation of propane within the process although it is preferred to remove the propane included in the feed of line 1 by withdrawing it with the oligomer product being removed via line 19. Normally the entire amount of material withdrawn from the overhead receiver 14 through line 15 will be divided between a first portion which is recycled to the reactor through line 2 and a second portion which is passed into the rectified flash vessel 8 through line 16 as reflux.

The cooling required in the process is preferably supplied by a stream of water flowing through line 20. The water first passes through the indirect heat exchange means 10 employed as an overhead condenser of the rectified flash vessel and then is passed through the indirect heat exchange means 24 employed to cool the reactor effluent stream. A portion of the cooling water of line 20 may bypass the indirect heat exchange means 24 through line 22 at a rate controlled by valve means 23.

The operation of the rectified flash vessel 8 may normally be adjusted to control the concentration of propane present in the liquid phase stream withdrawn from the process in line 19. It would therefore not be necessary to withdraw propane through line 25. The pressure within the flash vessel is preferably controlled by adjustment of valve 6 to achieve the desired degree of vaporization. This may be performed through use of a level control means 26 in receiver 14, which transmits a signal through means 26. However, as shown in the Drawing another variation in the flow scheme is the use of the optional reboiling means 18 which would vaporize a portion of the liquid phase removed from the vessel in line 17. The requirement for the use of such a reboiling means is basically determined by the conditions at which the vessel is to be operated and the desired minimum $C_3$ content of a liquid withdrawn from the bottom of the vessel.

A further variation to the flow of the subject process would be the replacement of the rectified flash vessel with a simple flash vessel which does not contain rectification equipment located within the upper portion of the vessel. Still further modification of the process shown in the Drawing is possible by employing two or more separate reactors operated either in parallel or in serial flow. It is also readily apparent that the cooling of the liquid phase material flowing through line 5 may be conducted in various manners, with one indirect heat exchange means being employed to cool effluent streams from two or more separate reactors which have been combined or with two or more exchangers being used to cool the effluent of a single reactor.

From this description it may be readily ascertained that several characteristic advantages are provided by the subject invention. First, the invention provides a coolant stream having a sufficiently high flow rate that good control of the reactor temperature is provided. Secondly, the subject process would not be seriously troubled or interfered with by leakage which would occur in any of the conduits 21. Such leakage would not seriously contaminate either the reactant stream flowing through the conduits or the coolant media flowing outside of the conduits with components having deleterious effects on the overall process. The only effect of leakage of the conduits 21 is a minor reduction in the overall efficiency of the process by allowing a portion of the feed stream to bypass an intended portion of the catalyst bed. Third, it may be observed that the heat removed from the reactor is employed directly in heating the reactants prior to their being passed into the flash vessel 8. Therefore, the heat removed from the reactor is used to enhance the degree of vaporization which may be achieved in the vessel as part of the separation process without the use of an external heat source. This efficient use of heat released by the exothermic oligomerization reaction, of heat transfer fluids and of heat exchange equipment point out the advantages of the subject invention. Further, it may be seen that the temperature control of the reactor is somewhat self-balancing in that an increase in the feed rate results in an equivalent automatic increase in the coolant flow rate. Only a single external coolant stream, preferably water, is required in the process although other fluids including process streams can be used.

It is contemplated that the subject process could be operated with the reactant effluent which is passing through the shell side of the reactor to serve as coolant not being measurably vaporized therein. However, it is preferred that the fluid entering line 7 is a mixed phase vapor-liquid stream. This embodiment of the invention would resemble those systems previously described wherein water used as a coolant is allowed to vaporize. The flow rate of the reactor effluent stream through the shell side of the reactor is expected to be great enough that only a portion of this material may be vaporized by the heat released in the reaction. Therefore, it is not contemplated to operate the process in a manner which would produce a totally vapor phase material entering line 7 for passage to the separation vessel.

The extent of vaporization of the coolant within the reactor can be controlled by adjustment of the reactor operating pressure. The fluid on the shell side of the reactor may be at substantially the same pressure as the reactants flowing through the tubular conduits 21 except for the inherent pressure drop incurred in the passage of the fluid through line 5 and the indirect heat exchange means 24. However, it is greatly preferred to provide a pressure control valve means 6 in line 5 such that the pressure of the coolant on the shell side of the reactor would be substantially less than the pressure of the reactants flowing through the conduits 21. Such a system is preferred since it is desirable to maintain liquid phase conditions within the catalyst containing portion of the reactor. It is therefore preferred that the catalyst bed or reactor effluent stream is depressurized by at least 69 KPa (10 psi) prior to being passed into the reaction vesssel as said coolant media. The effluent stream can be reduced in pressure by about 140 to about 4000 KPa during passage through the process lines, heat exchanger and valve prior to being returned to the reaction vessel.

Yet another variation or embodiment to the subject process, which is not preferred, would be the placement of the catalyst outside of the tubular conduits 21 with the reactants then passing initially through the shell side of the reactor prior to emerging for cooling. The cooled effluent of the reactor would then be returned to the reactor and passed through the conduits 21 to act as coolant.

An oligomerization process may be performed using several different types of catalyst within the reaction zone. For instance, U.S. Pat. Nos. 3,932,553 and 3,997,621 describe processes in which boron trifluoride is utilized as a catalyst. Both of these catalytic systems utilize a minor amount of an additive to control the extent to which the reaction proceeds. In both of these references, the catalyst system appears to be homogeneous. Other homogeneous catalyst systems comprising $BF_3$ and a promoter are described in U.S. Pat. Nos. 4,434,308; 4,413,156 and 4,395,578. Friedel-Crafts catalysts in general are often effective at dimerization. Aluminum trichloride ($AlCl_3$) promoted with a small amount of water or other hydroxy compound can be employed. Promoters or catalyst components which are vaporous at the conditions of the separation vessel 8 can be recycled as vapor drawn off this vessel or condensed into the recycle stream.

It is highly preferred that a heterogeneous catalyst system is employed. Heterogeneous catalytic systems for the production of higher molecular weight olefins by the oligomerization or dimerization of light olefins are described in U.S. Pat. Nos. 3,906,053; 3,916,019; 3,959,400; 3,981,940; 3,981,941; 4,365,105; 4,394,296; and 4,476,342. U.S. Pat. No. 4,400,565 describes a patent system comprising a cationic ion exchange resin and added boron trifluoride. As may be expected from the large number of catalysts, the conditions employed within the reaction zone may vary widely. For instance, the just cited references specify that the reaction may be performed at temperatures ranging from −50 degrees to 250 degrees Celsius and at a pressure ranging from about 1.3 to approximately 100 atmospheres gauge.

A widely used catalyst is the SPA (solid phosphoric acid) type catalyst. As used herein, the term "SPA catalyst" is intended to indicate a solid catalyst which contains as one of its principal ingredients an acid of phosphorus such as an ortho-, pyro- or tetra-phosphoric acid. The catalyst is normally formed by mixing the acid of phosphorus with a siliceous, solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives, such as mineral talc, fullers earth and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this such as a lower phosphoric acid content are however possible. Further details as to the composition, production, and use of SPA catalysts may be obtained from U.S. Pat. Nos. 3,050,472; 3,050,473; 3,132,109; 4,334,118 and from other references. Any of the above mentioned catalyst systems, and also those which are yet to be developed, may be employed in the subject process.

The catalyst is preferably disposed in fixed beds in the tubular type reactor structure. The catalyst is placed in relatively small diameter cylindrical tubes which are surrounded by the shell of the outer vessel. The coolant circulates inside the shell to remove the heat liberated by the exothermic reaction within the tubes. The individual tubes are preferably between about 1 and 10 cm in diameter and between 4 and 20 meters in length. An individual reactor will normally contain at least 40 such tubes. The temperature of the reactants is preferably also controlled by recycling relatively inert hydrocarbons (propane) which act as a heat sink. The tubular-form conduits containing the catalyst beds are preferably contained within a single, cylindrical, vertically oriented vessel, and the feed stream preferably enters the top of the reactor. Separate parallel or series reactors may be used in large process units.

The reaction zone may be maintained at widely varying conditions due to the previously listed variables including the use of different catalysts. A broad range of suitable pressures for oligomerization is from about 105 to 8400 kPag, with a preferred pressure range for an SPA catalyst being from 3000 to 8500 kPag. The pressure is preferably at least sufficiently high to maintain liquid phase conditions within the reaction zone. The temperature maintained in this zone with the preferred SPA catalyst may vary from about 120 to about 260 degrees Celsius with a temperature of from 150 to 225 degrees Celsius being preferred. Steam or water may be fed into the reactor to maintain the desired water content in the preferred catalyst. The total liquid hourly space velocity of combined feed through the catalyst bed is preferably between 0.5 and 3.0 hr$^-$.

In the preferred embodiment the process is utilized to form a product containing primarily $C_6$ and $C_9$ olefinic acyclic hydrocarbons having boiling points within a gasoline boiling point range of about 43 to about 215 degrees Celsius as determined by the appropriate ASTM distillation method. The feed stream may be heated by first being heat exchanged with the reactor effluent or the product stream prior to being further heated and passed into the top of the reactor.

The liquid-phase stream recovered from the reaction zone effluent stream in the separation vessel is preferably passed into an intermediate point of a fractionation column referred to as a debutanizer. One function of the debutanizer is to concentrate all of the $C_5$-plus hydrocarbons which enter the column into a net bottoms stream which is substantially free of $C_4$ hydrocarbons. The net bottoms stream of the fractionation column will therefore contain substantially all of any pentanes, hexanes, hexenes, nonanes or nonenes which enter the column. In a commercial unit this bottoms stream comprises a wide variety of hydrocarbons containing up to 15 carbon atoms per molecule. These hydrocarbons are primarily olefinic and may be used directly as a gasoline blending component. However, if desired they could be passed into a catalytic hydrogenation zone to effect their saturation. When properly designed and operated a reboiled column having about 40 real trays will function well as the debutanizing column. Essentially all of the propylene, propane, butane and butylene entering the debutanizing column is concentrated into the overhead vapor stream. Representative conditions for this overhead vapor stream as it is removed from the column include a pressure of about 1750 kPag (254 psig) and a temperature of about 49 degrees Celsius (120 degrees Fahrenheit).

The preferred embodiment of the invention may be characterized as a catalytic oligomerization process which comprises the steps of passing a hereinafter characterized recycle stream and a liquid-phase feed stream comprising propane and propylene or butanes and butylenes into a catalytic reaction zone within a reaction vessel and producing a reaction zone effluent stream comprising $C_6$-plus acyclic product hydrocarbons and propane or butane, with the reaction zone comprising a catalyst retaining means having an external heat exchange surface in contact with a mixedphase coolant media which circulates through the reaction vessel, with a portin of the coolant media being vaporized within the reaction vessel by heat removed from the catalyst retaining means; cooling the reaction zone effluent stream by indirect heat exchange against a first cooling stream; passing the reaction zone effluent stream through the reaction vessel as said coolant media and removing heat from said catalyst retaining means; passing a coolant media stream withdrawn from the reaction vessel into a separation zone comprising at least a rectification section and operated at conditions effective to separate the entering coolant media stream into an overhead vapor stream comprising propane or butane and a net bottoms stream comprising the product hydrocarbon; at least partially condensing the overhead vapor stream by indirect heat exchange against a second cooling stream, and returning a first portion of the resultant condensate to the separation zone as reflux and passing a second portion of the resultant condensate into the reaction zone as the previously referred to recycle stream; and, employing at least a portion of the second cooling stream as the previously referred to first cooling stream.

The following is an example of the subject process. A feed stream comprising an admixture of about 362 moles per hour of propylene and 120 moles per hour of propane is admixed with a recycle stream having a flow rate of approximately 960 moles per hour. This liquid phase admixture is passed into a single vertical reactor and divided between the individual tubular catalyst containing conduits. The admixture enters the reactor at a temperature of about 140 degrees Celsius and a pressure of 7500 kPag. A large portion of the propylene is converted to $C_6$ and $C_9$ oligomers within the reactor. The effluent of the reactor emerges at a temperature of approximately 180 degrees Celsius. The total effluent is cooled by indirect heat exchange to about 150 degrees Celsius and then depressurized. The thus cooled hydrocarbons are then passed into the shell side of the reactor vessel to act as coolant having a presure of about 3200 kPag. The coolant hydrocarbons emerge from the shell side of the reactor at a temperature of about 110 degrees Celsius as a mixed-phase stream. They are then passed into a rectified flash vessel at a point below five fractionation trays. The overhead vapor of the vessel has a pressure of about 1500 kPag. As illustrated in the Drawing, this vapor is condensed to form the liquid used as reflux and as the recycle stream. The recycle stream will normally contain less than six percent propylene. The bottoms liquid stream removed from the flash vessel will have a flow rate of about 258 moles per hour. This liquid stream is passed into a debutanizer column which separates the liquid stream into a net overhead stream, which is an LPG product stream, and a net bottoms product stream containing the $C_6$ and $C_9$ oligomers. The net debutanizer bottoms stream will have a flow rate of about 130 moles per hour. The overhead vapor stream of the separation vessel is condensed by indirect heat exchange against a stream of cooling water. This cooling water stream is then passed through the indirect heat exchanger used to remove heat from the reactants between their tube side and shell transits through the reactor.

I claim as my invention:

1. A catalytic oligomerization process which comprises the steps:
   (a) passing a liquid-phase feed stream comprising a $C_2$–$C_5$ aliphatic feed olefinic hydrocarbon into contact with an oligomerization catalyst within a reaction vessel and producing a reaction zone effluent stream comprising the feed hydrocarbon and a $C_6$-plus product hydrocarbon, with the reaction zone comprising a tubular catalyst retaining means which is in indirect heat exchange relationship with a coolant media which is vertically circulated through the reaction vessel to remove heat released in the oligomerization reaction, with a portion of the coolant media being vaporized within the reaction vessel;
   (b) cooling the reaction zone effluent stream by indirect heat exchange against a cooling stream;
   (c) passing the reaction zone effluent stream through the reaction vessel as said coolant media; and,
   (d) passing coolant media withdrawn from the reaction vessel into a separation zone operated at conditions effective to separate the entering hydrocarbons into an overhead vapor stream comprising the feed hydrocarbon and a net bottoms liquid stream comprising the product hydrocarbon which is removed from the process as a product stream.

2. The process of claim 1 further characterized in that condensate is produced by at least partially condensing the overhead vapor stream, a first portion of the condensate is passed into the separation zone as reflux, and a second portion of the condensate is passed into the reaction zone as a recycle stream.

3. The process of claim 1 further characterized in that the feed olefinic hydrocarbon is a $C_3$ or $C_4$ hydrocarbon.

4. The process of claim 3 further characterized in that the product hydrocarbon is an olefinic hydrocarbon.

5. The process of claim 1 further characterized in that the reaction zone effluent stream is reduced in pressure by at least 69 kPa prior to being passed into the reaction vessel as said coolant media.

6. A process for the catalytic oligomerization of light olefinic hydrocarbons which comprises the steps of:
   (a) passing a hereinafter characterized recycle stream and a liquid-phase feed stream comprising propane and propylene or butanes and butylenes into a catalytic reaction zone located within a vertical reaction vessel and producing a reaction zone effluent stream comprising $C_6$-plus acyclic product hydrocarbons and propane or butane, with the reaction zone comprising a catalyst retaining means having an external heat exchange surface in contact with a mixed-phase coolant media which circulates through the reaction vessel, with a portion of the coolant media being vaporized within the reaction vessel by heat removed from the catalyst retaining means;

(b) cooling the reaction zone effluent stream by indirect heat exchange against a first cooling stream;

(c) passing the reaction zone effluent stream through the reaction vessel as said coolant media and removing heat from said catalyst retaining means;

(d) passing a coolant media stream withdrawn from the reaction vessel into a separation zone comprising at least a rectification section and operated at conditions effective to separate the coolant media stream into an overhead vapor stream comprising propane or butane and a net bottoms stream comprising the product hydrocarbon; and, (e) at least partially condensing the overhead vapor stream by indirect heat exchange against a second cooling stream, and returning a first portion of the resultant condensate to the separation zone as reflux and passing a second portion of the resultant condensate into the reaction zone as the previously referred to recycle stream.

7. The process of claim 6 further characterized in that the reaction zone contains a solid oligomerization catalyst.

8. The process of claim 7 further characterized in that the feed stream is rich in $C_3$ hydrocarbons.

9. The process of claim 7 further characterized in that the feed stream is rich in $C_4$ hydrocarbons.

10. The process of claim 6 further characterized in that the catalyst retaining means comprises cylindrical tubular conduits which contain solid oligomerization catalyst particles, and in that the coolant media is circulated over the outer side of the tubular conduits after being cooled by indirect heat exchange.

11. The process of claim 6 further characterized in that at least a portion of the second cooling stream is employed as said first cooling stream.

12. The process of claim 11 further characterized in that the second cooling stream comprises water.

13. The process of claim 6 further characterized in that the reaction zone effluent is depressurized by at least 69 kPa prior to being passed through the reaction vessel as said coolant media.

14. The process of claim 13 further characterized in that the feed stream comprises a mixture of propylene and propane.

15. The process of claim 13 further characterized in that the depressurization of the reaction zone effluent stream results in a partial vaporization of the reaction zone effluent stream.

* * * * *